United States Patent
Kato et al.

(10) Patent No.: US 9,763,560 B2
(45) Date of Patent: Sep. 19, 2017

(54) ENDOSCOPE SYSTEM AND ELECTROSTATIC COUPLING

(75) Inventors: Shuichi Kato, Tokyo (JP); Susumu Kawata, Tokyo (JP); Makoto Honda, Odawara (JP)

(73) Assignee: OLYMPUS CORPORATION, Tokyo (JP)

( * ) Notice: Subject to any disclaimer, the term of this patent is extended or adjusted under 35 U.S.C. 154(b) by 578 days.

(21) Appl. No.: 13/277,685

(22) Filed: Oct. 20, 2011

(65) Prior Publication Data

US 2012/0088970 A1 Apr. 12, 2012

Related U.S. Application Data

(63) Continuation of application No. PCT/JP2010/002822, filed on Apr. 19, 2010.

(30) Foreign Application Priority Data

Apr. 21, 2009 (JP) .................................. 2009-102961

(51) Int. Cl.
*A61B 1/00* (2006.01)
*A61B 1/05* (2006.01)
(Continued)

(52) U.S. Cl.
CPC ...... *A61B 1/00114* (2013.01); *A61B 1/00124* (2013.01); *A61B 1/00126* (2013.01);
(Continued)

(58) Field of Classification Search
CPC .............. A61B 1/00124; A61B 1/0669; A61B 1/00039; A61B 1/00128
(Continued)

(56) References Cited

U.S. PATENT DOCUMENTS 4,331,403 A  5/1982  Ohno
4,402,313 A * 9/1983  Yabe .................. A61B 1/00117
                                                600/132

(Continued)

FOREIGN PATENT DOCUMENTS

CN     1826078 A    8/2006
CN   101282679 A   10/2008
(Continued)

OTHER PUBLICATIONS

International Search Report of PCT/JP2010/002822, mailing date May 25, 2010.
(Continued)

*Primary Examiner* — John P Leubecker
*Assistant Examiner* — Rajaa El Alami
(74) *Attorney, Agent, or Firm* — Westerman, Hattori, Daniels & Adrian, LLP

(57) ABSTRACT

An endoscope system includes: an endoscope scope insertion portion having an insertion portion configured to be inserted inside a living organism; an extracorporeal device which is disposed outside the living organism; a first scope-side signal connecting portion that is provided on the endoscope scope insertion portion and has a first electrode; and a cylindrical first extracorporeal-side signal connecting portion that is provided on the extracorporeal device and has a second electrode, the first extracorporeal-side signal connecting portion configured to engage with the first scope-side signal connecting portion. In this endoscope system, when the first scope-side signal connecting portion is engaged with the first extracorporeal-side signal connecting portion, at least a portion of the first scope-side signal connecting portion is located within an inside-cylinder space of the first extracorporeal-side signal connecting portion, (Continued)

and the first electrode and the second electrode are electrostatically coupled together.

9 Claims, 9 Drawing Sheets

(51) Int. Cl.
    *A61B 1/07*     (2006.01)
    *A61B 1/12*     (2006.01)
    *A61B 1/06*     (2006.01)

(52) U.S. Cl.
    CPC ............ *A61B 1/00128* (2013.01); *A61B 1/05* (2013.01); *A61B 1/0669* (2013.01); *A61B 1/07* (2013.01); *A61B 1/121* (2013.01)

(58) Field of Classification Search
    USPC .................................................. 600/132, 133
    See application file for complete search history.

(56) References Cited

U.S. PATENT DOCUMENTS

| | | | | |
|---|---|---|---|---|
| 6,095,970 | A * | 8/2000 | Hidaka | A61B 1/00124 600/109 |
| 6,099,465 | A * | 8/2000 | Inoue | A61B 1/05 348/75 |
| 8,075,477 | B2 * | 12/2011 | Nakamura | A61B 1/0011 439/67 |
| 8,088,064 | B2 * | 1/2012 | Itoi | A61B 1/00128 600/131 |
| 8,529,439 | B2 * | 9/2013 | Ito | A61B 1/012 600/112 |
| 8,708,211 | B2 * | 4/2014 | Zemlok | A61B 17/07207 227/175.1 |
| 8,758,233 | B2 * | 6/2014 | Masaki | A61B 1/00039 600/131 |
| 9,615,826 | B2 * | 4/2017 | Shelton, IV | A61B 17/068 |
| 2005/0228268 | A1 * | 10/2005 | Cole | A61B 5/1112 600/420 |
| 2006/0116550 | A1 * | 6/2006 | Noguchi et al. | 600/132 |
| 2006/0116552 | A1 | 6/2006 | Noguchi et al. | |
| 2008/0269560 | A1 * | 10/2008 | Ito | A61B 1/00105 600/132 |
| 2008/0281157 | A1 * | 11/2008 | Miyagi | A61B 1/00126 600/132 |
| 2009/0058997 | A1 * | 3/2009 | Kato | 348/65 |

FOREIGN PATENT DOCUMENTS

| | | |
|---|---|---|
| JP | 10-155740 A | 6/1998 |
| JP | 2006-320381 A | 11/2006 |
| JP | 2007-097767 A | 4/2007 |
| JP | 2009-056240 A | 3/2009 |
| JP | 2009-061032 A | 3/2009 |
| WO | 2005/077249 A1 | 8/2005 |
| WO | 2005/077250 A1 | 8/2005 |

OTHER PUBLICATIONS

Office Action dated Oct. 15, 2013, issued in Chinese application No. 201080016697.1, with English translation.

Extended European Search Report dated Aug. 8, 2014, issued in corresponding European Patent Application No. 10766832.9 (7 pages).

* cited by examiner

ENDOSCOPE SYSTEM AND ELECTROSTATIC COUPLING

This application is a continuation application based on a PCT Patent Application No. PCT/JP2010/002822, filed Apr. 19, 2010, whose priority is claimed on Japanese Patent Application No. 2009-102961, filed Apr. 21, 2009, the contents of both the PCT Application and the Japanese Application are incorporated herein by reference.

BACKGROUND OF THE INVENTION

Field of the Invention

The present invention relates to an endoscope system that transmits signals by means of electrostatic coupling.

Description of Related Art

Typically, in an endoscope system there are provided an endoscope scope insertion portion that has an insertion portion which is inserted inside a living organism, and an extracorporeal device such as a monitor which is disposed outside the organism. In order for signals to be transmitted from one of these to the other, electrodes are provided on both the endoscope scope insertion portion and the extracorporeal device, and control signals and video signals and the like are transmitted by placing these electrodes in direct contact with each other.

Here, because body fluids and the like of the organism become adhered to the insertion portion when the insertion portion is inserted inside the organism, after such use it is necessary for the insertion portion and the like to be disinfected and sterilized using a disinfecting solution or the like. At this time, if any disinfecting solution is not wiped off but remains on a sterilized electrode, there is a possibility that this electrode will become corroded.

Therefore, as is shown in, for example, Japanese Patent Application, First Publication No. 2007-97767, an electronic endoscope system has been proposed in which signals are transmitted by means of electrostatic coupling without electrodes being placed in direct contact with each other.

In this electronic endoscope system, a universal cord which is provided on the endoscope scope insertion portion is connected to the extracorporeal device. A pair of connectors (i.e., signal connecting portions) which are capable of being removably connected to each other is provided at a connecting portion between the universal cord and the extracorporeal device.

On the connector on the endoscope scope insertion portion side, there are provided a circular first pad (i.e., electrode) which is positioned at a center portion of the connector, and a toroidal second pad which is positioned surrounding this first pad. In addition, on the connector on the extracorporeal device side, there are provided a third pad which is positioned at a center portion of the connector, and a toroidal fourth pad which is positioned surrounding this third pad.

When the pair of connectors has been fitted together, the first pad and the third pad, and the second pad and the fourth pad respectively face in the direction in which the universal cord extends, and in this state the mutually facing pads approach each other.

Image information about the interior of the organism is transmitted from the endoscope scope insertion portion to the extracorporeal device by the electrostatic coupling between the first pad and the third pad, and control signals and the like are transmitted from the extracorporeal device to the endoscope scope insertion portion by the electrostatic coupling between the second pad and the fourth pad.

In this electronic endoscope system, the first pad and the third pad are covered by an insulating material. As a result, even if the endoscope scope insertion portion is cleaned using a disinfecting solution, these pads can be prevented from corroding, and corrosion of the endoscope scope insertion portion is also prevented since the task of washing the endoscope scope insertion portion is made easier.

SUMMARY OF THE INVENTION

The endoscope system according to an aspect of the present invention is provided with: an endoscope scope insertion portion having an insertion portion that is configured to be inserted inside a living organism and is provided with an observation device which is capable of making observations on the distal end side thereof; an extracorporeal device which is disposed outside the living organism; a first scope-side signal connecting portion that is provided on the endoscope scope insertion portion and has a first electrode which is electrically connected to the endoscope scope insertion portion; and a cylindrical first extracorporeal-side signal connecting portion that is provided on the extracorporeal device and has a second electrode which is electrically connected to the extracorporeal device, the first extracorporeal-side signal connecting portion configured to engage with the first scope-side signal connecting portion, wherein when the first scope-side signal connecting portion is engaged with the first extracorporeal-side signal connecting portion, at least a portion of the first scope-side signal connecting portion is located within an inside-cylinder space of the first extracorporeal-side signal connecting portion, so that the first electrode and the second electrode are electrostatically coupled together.

Note that the term "cylindrical shape" in the present specification refers not only to shapes which are round, long, and hollow, but also to shapes in which a part of a wall-shaped portion that encircles a hollow center portion has been cut away, namely, to what are substantially C-shapes when viewed from the longitudinal direction of the cylinder.

In the above described endoscope system, it is more preferable for there to be further provided: a scope-side power connecting portion that is provided on the endoscope scope insertion portion and has a first coil which is electrically connected to the endoscope scope insertion portion; and a cylindrical extracorporeal-side power connecting portion that is provided on the extracorporeal device and has a second coil which is electrically connected to the extracorporeal device, the extracorporeal-side power connecting portion configured to engage with the scope-side power connecting portion, and when the scope-side power connecting portion is engaged with the extracorporeal-side power connecting portion, it is preferable for at least a portion of the scope-side power connecting portion to be located within an inside-cylinder space of the extracorporeal-side power connecting portion, so that the first coil and the second coil are electromagnetically coupled together.

In the above described endoscope system, it is more preferable for there to be further provided: a second scope-side signal connecting portion that is provided on the endoscope scope insertion portion and has a third electrode which is electrically connected to the endoscope scope insertion portion; and a cylindrical second extracorporeal-side signal connecting portion that is provided on the extracorporeal device and has a fourth electrode which is electrically connected to the extracorporeal device, the second extracorporeal-side signal connecting portion configured to engage with the second scope-side signal connecting portion, and when the second scope-side signal connecting portion is engaged with the second extracorporeal-side signal connecting portion, it is preferable for at least a portion of the second scope-side signal connecting portion to be located within an inside-cylinder space of the second extracorporeal-side signal connecting portion, so that the third electrode and the fourth electrode are electrostatically coupled together, and for signals that are based on the electrostatic coupling between the third electrode and the fourth electrode to have an opposite phase relative to signals that are based on the electrostatic coupling between the first electrode and the second electrode.

In the above described endoscope system, it is more preferable for the endoscope scope insertion portion to be configured such that it is able to rotate around the axis of the first extracorporeal-side signal connecting portion relative to the extracorporeal device.

In the above described endoscope system, it is more preferable for there to be further provided a solid or liquid dielectric material whose relative dielectric constant is greater than 1, and when the first scope-side signal connecting portion and the first extracorporeal-side signal connecting portion are engaged with each other, it is preferable for the dielectric material to be located between the first electrode and the second electrode.

In the above described endoscope system, it is more preferable for the first scope-side signal connecting portion to be formed in a cylindrical shape, and to have an inside-cylinder space formed inside it.

In the above described endoscope system, it is more preferable for there to be further provided a light guide which is inserted in the inside-cylinder space of the first scope-side signal connecting portion.

In the above described endoscope system, it is more preferable for the scope-side power connecting portion to be formed in a cylindrical shape, and to have an inside-cylinder space formed inside it, and for the first scope-side signal connecting portion to be disposed outside the inside-cylinder space of the scope-side power connecting portion.

In the above described endoscope system, it is more preferable for the scope-side power connecting portion to be formed in a cylindrical shape, and to have an inside-cylinder space formed inside it, and for either all of or a portion of the first scope-side signal connecting portion to be disposed within the inside-cylinder space of the scope-side power connecting portion.

DETAILED DESCRIPTION OF THE INVENTION

First Embodiment

Figure 1:
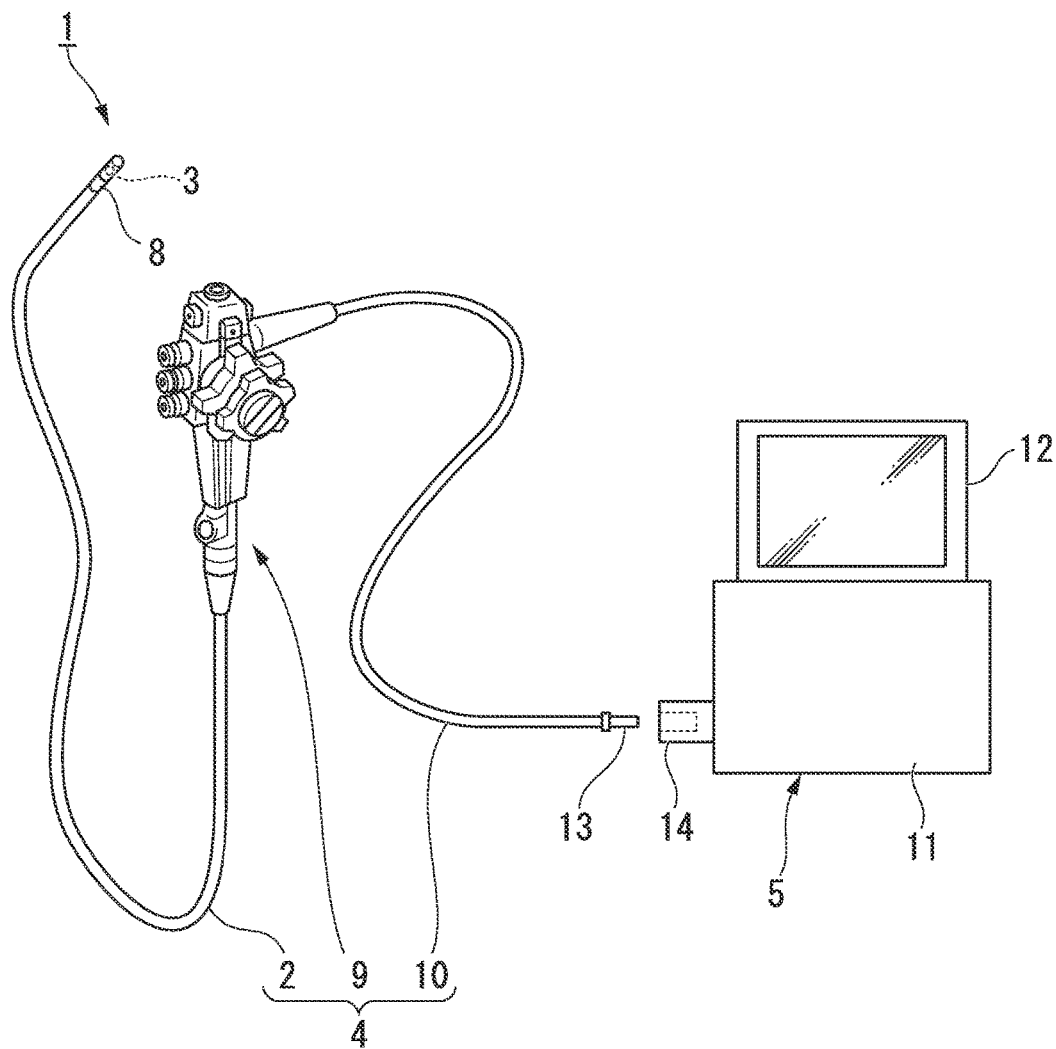
FIG. 1 is a view showing the overall structure of an endoscope system according to a first embodiment of the present invention.

A first embodiment of an endoscope system according to the present invention will now be described with reference made to FIG. 1 through FIG. 7. As is shown in FIG. 1, this endoscope system 1 is an apparatus which inserts an insertion portion 2 into a living organism, and observes the interior of the organism.

The endoscope system 1 of the present embodiment is provided with an endoscope scope insertion portion 4 which has an insertion portion 2 which is provided with a CCD (i.e., an observation device) 3 which is capable of making observations on the distal end side thereof, and an extracorporeal device 5 which is disposed outside the organism.

The endoscope scope insertion portion 4 is provided with the insertion portion 2 which is formed from a flexible material and which is provided with a bending portion 8 on the distal end side thereof, an operating portion 9 which is attached to a proximal end portion of the insertion portion 2 and which is provided with an angle knob or the like which is used to make the bending portion 8 perform bending operations, and a universal cord 10 which connects together the operating portion 9 and the extracorporeal device 5.

An illumination device (not shown) such as, for example, a condensing optical system, and the CCD 3 are provided on a distal end portion of the insertion portion 2, namely, on the distal end side of the bending portion 8. The illumination device illuminates the distal end side of the insertion portion 2 using illumination light which is guided through a scope-side light guide 53 and an extracorporeal-side light guide 58 (described below).

The extracorporeal device 5 is provided with a main body 11 which serves as a base, and with a display unit 12 which displays video signals from the CCD 3. A scope-side connector 13 and an extracorporeal-side connector 14 are provided between a proximal end portion of the universal cord 10 and the main body 11. The scope-side connector 13 and the extracorporeal-side connector 14 are able to be connected to and disconnected from each other.

Note that in the present embodiment, because the scope-side connector 13 and the extracorporeal-side connector 14 are provided between the base end portion of the universal cord 10 and the main body 11, the universal cord 10 forms a part of the endoscope scope insertion portion 4. However, the scope-side connector and the extracorporeal-side connector may also be provided between a distal end portion of the universal cord 10 and the operating portion 9. In this case, the universal cord forms a part of the extracorporeal device 5.

Accordingly, the endoscope scope insertion portion is on the insertion portion 2 side of the connecting portion between the scope-side connector and the extracorporeal-side connector, while the extracorporeal device is on the main body 11 side thereof.

Moreover, the position where the set of the scope-side connector and the extracorporeal-side connector is provided is not particularly limited, and may also be midway along the universal cord 10 or midway along the insertion portion 2.

Figure 2:
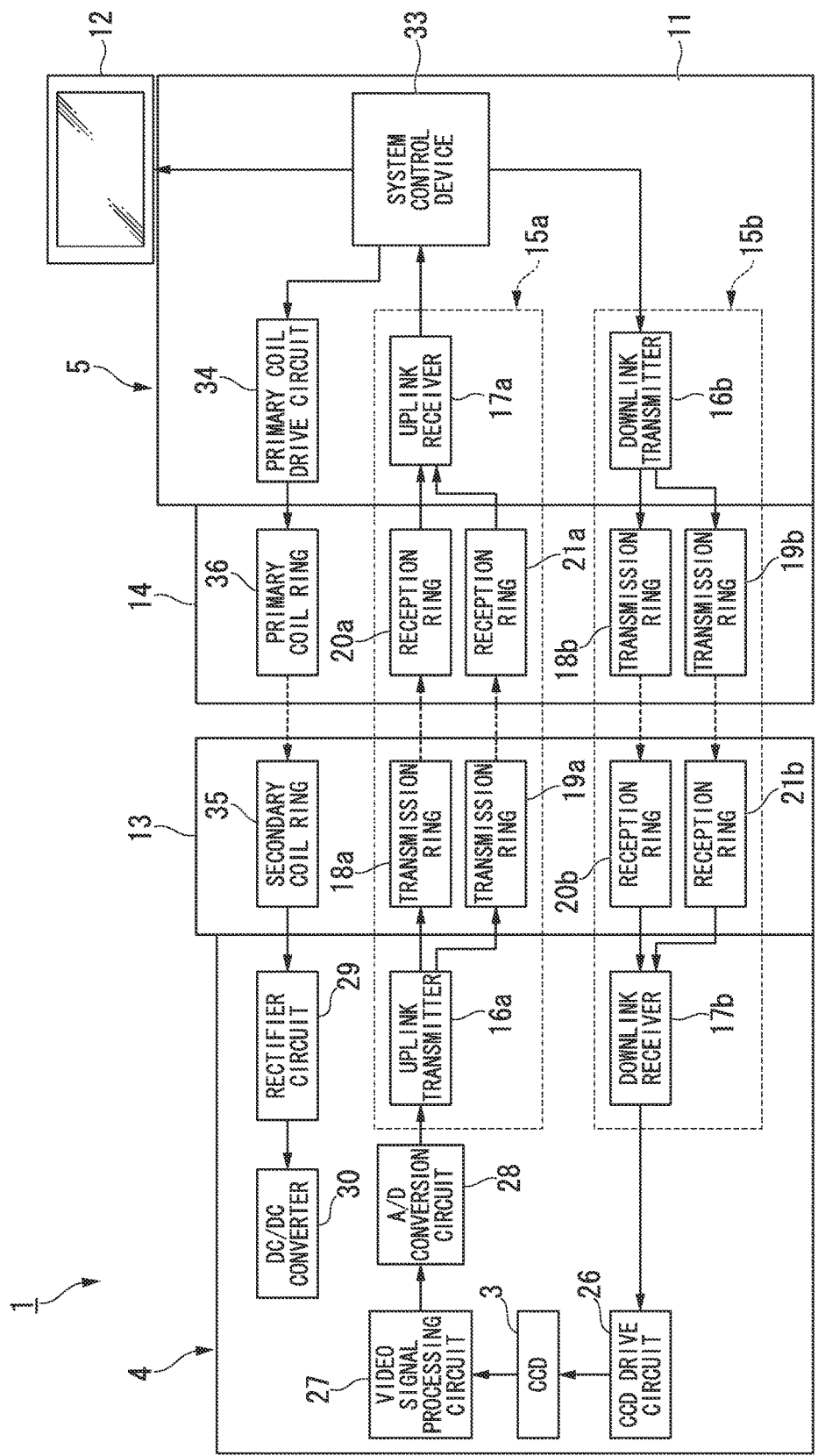
FIG. 2 is a block diagram showing the structure of this endoscope system.

As is shown in FIG. 2, the endoscope system 1 is provided with signal transmitters 15a and 15b that encode signals and then transmit them by means of electrostatic coupling, and that also decode transmitted signals. As is described below in detail, signals from the endoscope scope insertion portion 4 to the extracorporeal device 5 (i.e., in an uplink direction) are transmitted by the signal transmitter 15a, while signals from the extracorporeal device 5 to the endoscope scope insertion portion 4 (i.e., in a downlink direction) are transmitted by the signal transmitter 15b.

Because the signal transmitter 15a and the signal transmitter 15b are the same in structure, only the signal transmitter 15a will be described in detail. Note that the same numbers are used for the symbols which describe corresponding elements between the signal transmitter 15a and the signal transmitter 15b, and a distinction is made between them by attaching the letter "a" to elements of the signal transmitter 15a and the letter "b" to elements of the signal transmitter 15b.

The endoscope scope insertion portion 4 has a CCD drive circuit 26 that controls the drive state of the CCD 3, a video signal processing circuit 27 that processes image data (i.e., video signals) and the like acquired by the CCD 3, an A/D conversion circuit 28 that converts analog signals obtained by the video signal processing circuit 27 into digital signals, a rectifier circuit 29 that converts alternating current into direct current, and a DC/DC converter 30 that adjusts the voltage of the direct current.

In addition, the endoscope scope insertion portion 4 also has an uplink transmitter 16a that encodes and then transmit signals, and a downlink receiver 17b that decodes received signals.

The main body 11 of the extracorporeal device 5 has a system control device 33 that controls the endoscope scope insertion portion 4 and the extracorporeal device 5 and processes video signals, a primary coil drive circuit 34 that controls the drive state of a primary coil ring 36 (described below), an uplink receiver 17a that decodes received signals, and a downlink transmitter 16b that encodes signals and then transmits them.

The scope-side connector 13 has a secondary coil ring (i.e., a first coil) 35 to which power is supplied, a transmission ring (i.e., a first electrode) 18a and a transmission ring (i.e., a third electrode) 19a that transmit signals by means of electrostatic coupling, and a reception ring (i.e., a first electrode) 20b and a reception ring (i.e., a third electrode) 21b that receive signals by means of electrostatic coupling.

In addition, the extracorporeal-side connector 14 has a primary coil ring (i.e., a second coil) 36 which supplies power, a reception ring (i.e., a second electrode) 20a and a reception ring (i.e., a fourth electrode) 21a that receive signals by means of electrostatic coupling, and a transmission ring (i.e., a second electrode) 18b and a transmission ring (i.e., a fourth electrode) 19b that transmit signals by means of electrostatic coupling.

The signal transmitter 15a is constructed from the uplink transmitter 16a, the uplink receiver 17a, the transmission ring 18a, the transmission ring 19a, the reception ring 20a, and the reception ring 21a, while the signal transmitter 15b is constructed from the downlink transmitter 16b, the downlink receiver 17b the transmission ring 18b, the transmission ring 19b, the reception ring 20b, and the reception ring 21b.

Next, the structure of the signal transmitter 15a will be described in detail.

Figure 3:
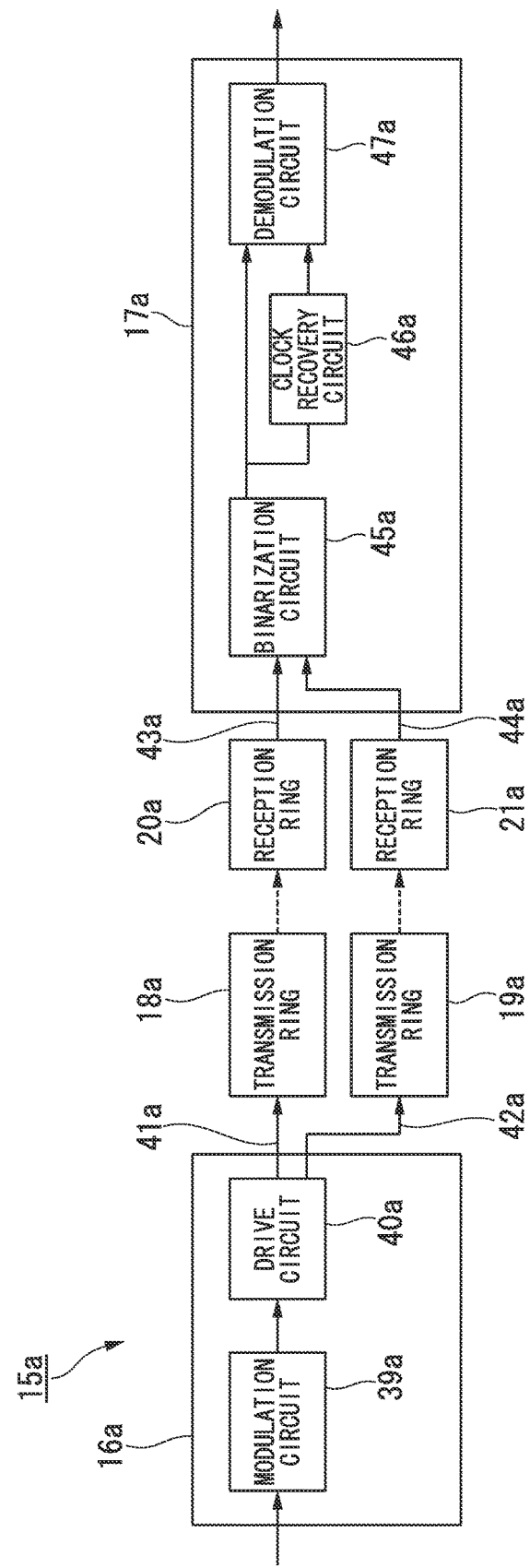
FIG. 3 is a block diagram showing the structure of a signal transmitter of this endoscope system.

As is shown in FIG. 3, the uplink transmitter 16a has a modulation circuit 39a that modulates digital signals (i.e. data) which are transmitted from the A/D conversion circuit 28 so as to perform Manchester encoding thereon, and a driver circuit 40a which is connected to the modulation circuit 39a. The driver circuit 40a outputs the current of the encoded data modulated by the modulation circuit 39a and the current of opposite phase data created from this encoded data respectively to a terminal of a transmission line 41a and a terminal of a transmission line 42a after amplifying and performing impedance conversion thereon.

The other terminals of the transmission lines 41a and 42a are electrically connected respectively to the transmission rings 18a and 19a. In addition, the reception rings 20a and 21a are electrically connected respectively to a terminal of a transmission line 43a and a terminal of a transmission line 44a.

The uplink receiver 17a has a binarization circuit 45a that is connected to the other terminals of the transmission lines 43a and 44a and detects the level of each data item, a clock recovery circuit 46a that is connected to the binarization circuit 45a and recovers clocks from the encoded data, and a demodulation circuit 47a that is connected to the binarization circuit 45a and the clock recovery circuit 46a and performs demodulation on the encoded data.

Video signals demodulated by the demodulation circuit 47a are transmitted to the system control device 33.

Next, the structures of the scope-side connector 13 and the extracorporeal-side connector 14 will be described.

Figure 4:
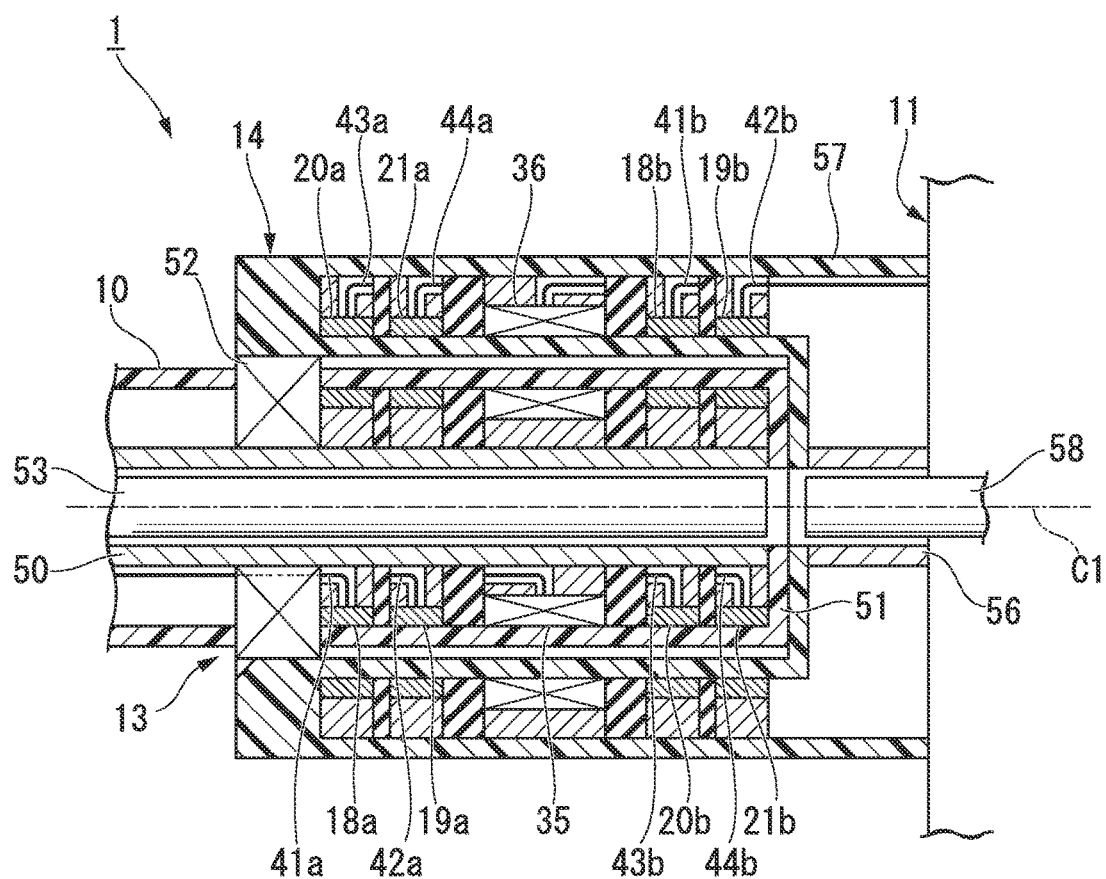
FIG. 4 is a cross-sectional view showing a state in which a scope-side connector and an extracorporeal-side connector of this endoscope system are connected together.

As is shown in FIG. 4, the scope-side connector 13 is formed in a circular cylindrical shape, and the extracorporeal-side connector 14 is formed in a circular cylindrical shape to encircle the outer circumferential surface of the scope-side connector 13. By engaging the scope-side connector 13 with the extracorporeal-side connector 14, the scope-side connector 13 and the extracorporeal-side connector 14 are connected together, and by releasing this engagement, the scope-side connector 13 and the extracorporeal-side connector 14 are separated from each other. Note that when the scope-side connector 13 has been connected to the extracorporeal-side connector 14, the two of them are aligned on a common axis (i.e., the cylinder axis) C1.

The scope-side connector 13 is provided with a scope-side shaft component 50 which is formed in a cylindrical shape and is aligned on the axis C1, the transmission rings 18a and 19a, the reception rings 20b and 21b, and the secondary coil ring 35 which are all formed in a circular cylindrical shape, a scope-side covering component 51 which is formed from a dielectric material and is provided such that it covers outer circumferential surfaces and also end portions of the transmission rings 18a and 19a, the reception rings 20b and 21b, and the secondary coil ring 35, and a bearing 52 which is formed in a ring shape.

The transmission rings 18a and 19a, the secondary coil ring 35, and the reception rings 20b and 21b are arranged such that they extend along the axis C1, and each of them is mounted on a supporting component that is formed from an insulating material.

The transmission rings 18a and 19a, the secondary coil ring 35, and the reception rings 20b and 21b are arranged in this order from the distal end side to the proximal end side of the scope-side shaft component 50, and each of them is mounted on the scope-side shaft component 50 via a supporting component. In addition, shielding components that are used to block any electromagnetic effects are provided respectively between the transmission ring 18a and the transmission ring 19a, between the transmission ring 19a and the secondary coil ring 35, between the secondary coil ring 35 and the reception ring 20b, and between the reception ring 20b and the reception ring 21b.

The bearing 52 is set such that it protrudes slightly onto the outer side in a radial direction from the scope-side covering component 51, and is slightly exposed. An outer circumferential surface and an inner circumferential surface of the bearing 52 are arranged such that they are aligned with the axis C1. The outer circumferential surface of the bearing 52 is able to rotate in a state of reduced friction force relative to the inner circumferential surface thereof around the axis C1.

The scope-side light guide 53 which guides illumination light to an illumination device (not shown) is inserted inside the scope-side shaft component 50.

Figure 5:
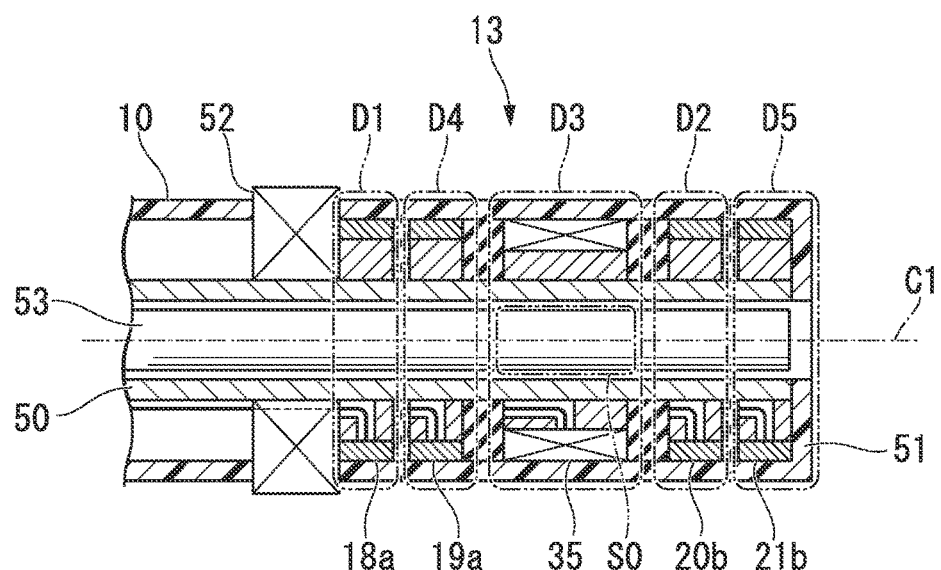
FIG. 5 is a cross-sectional view of the scope-side connector of this endoscope system.

As is shown in FIG. 5, the scope-side connector 13 has a structure in which first scope-side signal connecting portions D1 and D2 that respectively have the transmission ring 18a and the reception ring 20b which are the first electrodes, a scope-side power connecting portion D3 that has the secondary coil ring 35 which is the first coil, and second scope-side signal connecting portions D4 and D5 that respectively have the transmission ring 19a and the reception ring 21b which are the third electrodes are constructed integrally with each other.

The first scope-side signal connecting portions D1 and D2, the scope-side power connecting portion D3, and the second scope-side signal connecting portions D4 and D5 are all formed in a circular cylindrical shape, and all have the same inner diameter and outer diameter. In addition, they are disposed at offset positions relative to each other along the direction of the axis C1 so that the axis of each of them corresponds with the axis C1.

In other words, the first scope-side signal connecting portions D1 and D2 are placed on the outer side of an inside-cylinder space S0 which is a space formed inside the scope-side power connecting portion D3.

The description will now return to FIG. 4. The extracorporeal-side connector 14 is provided with an extracorporeal-side shaft component 56 which is formed in a cylindrical shape and is aligned on the axis C1, the reception rings 20a and 21a, the transmission rings 18b and 19b, and the primary coil ring 36 which are all formed in a circular cylindrical shape, and an extracorporeal-side covering component 57 which is formed from a dielectric material and is provided such that it covers inner circumferential surfaces, outer circumferential surfaces, and also end portions of the reception rings 20a and 21a, the transmission rings 18b and 19b, and the primary coil ring 36.

The reception rings 20a and 21a, the primary coil ring 36, and the transmission rings 18b and 19b are arranged such that they extend along the axis C1, and each of them is mounted on a supporting component that is formed from an insulating material.

The reception rings 20a and 21a, the primary coil ring 36, and the transmission rings 18b and 19b are arranged inside the extracorporeal-side covering component 57 such that they approach the main body 11 in this order. In addition, shielding components that are used to block any electromagnetic effects are provided respectively between the reception ring 20a and the reception ring 21a, between the reception ring 21a and the primary coil ring 36, between the primary coil ring 36 and the transmission ring 18b, and between the transmission ring 18b and the transmission ring 19b.

The extracorporeal-side light guide 58 which guides illumination light emitted from a light emitting device (not shown) which is provided inside the main body 11 is inserted inside the extracorporeal-side shaft component 56.

In the present embodiment, polycarbonate having a relative dielectric constant of 2.95 is used for the scope-side covering component 51 and the extracorporeal-side covering component 57.

When the scope-side connector 13 and the extracorporeal-side connector 14 are connected together, the transmission ring 18a is facing the reception ring 20a, the transmission ring 19a is facing the reception ring 21a, the secondary coil ring 35 is facing the primary coil ring 36, the reception ring 20b is facing the transmission ring 18b, and the reception ring 21b is facing the transmission ring 19b.

Figure 6:
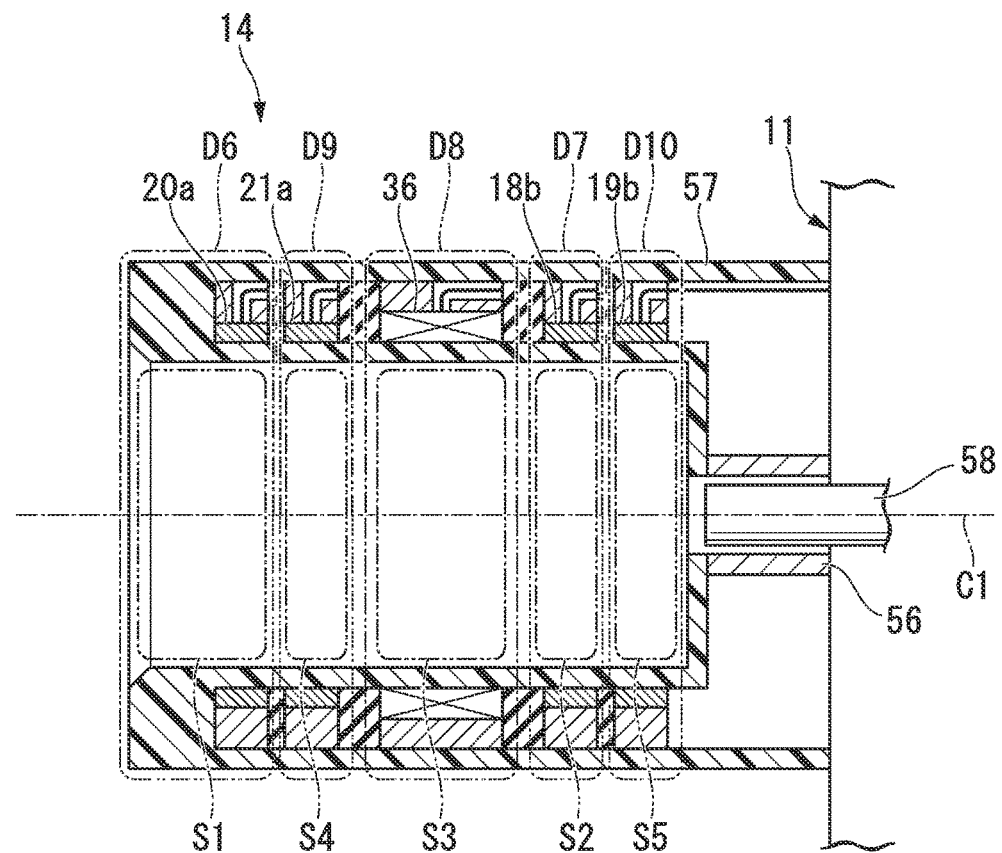
FIG. 6 is a cross-sectional view of the extracorporeal-side connector of this endoscope system.

As is shown in FIG. 6, the extracorporeal-side connector 14 has a structure in which first extracorporeal-side signal connecting portions D6 and D7 that respectively have the reception ring 20a and the transmission ring 18b which are the second electrodes, an extracorporeal-side power connecting portion D8 that has the primary coil ring 36 which is the second coil, and second extracorporeal-side signal connecting portions D9 and D10 that respectively have the reception ring 21a and the transmission ring 19b which are the fourth electrodes are formed integrally with each other.

The first extracorporeal-side signal connecting portions D6 and D7, the extracorporeal-side power connecting portion D8, and the second extracorporeal-side signal connecting portions D9 and D10 are all formed in a circular cylindrical shape, and all have the same inner diameter and outer diameter. In addition, they are arranged at offset positions relative to each other along the direction of the axis C1 so that the axis of each of them corresponds with the axis C1.

Accordingly, an inside-cylinder space S1 of the first extracorporeal-side signal connecting portion D6, an inside-cylinder space S2 of the first extracorporeal-side signal connecting portion D7, an inside-cylinder space S3 of the extracorporeal-side power connecting portion D8, an inside-cylinder space S4 of the second extracorporeal-side signal connecting portion D9, and an inside-cylinder space S5 of the second extracorporeal-side signal connecting portion D10 are disposed at offset positions in the direction of the axis C1 such that they do not overlap each other.

Moreover, as is shown in FIG. 4, when the inner circumferential surface of the extracorporeal-side covering component 57 is attached to the outer circumferential surface of the bearing 52 while the axis of the scope-side connector 13 is aligned with the axis of the extracorporeal-side connector 14, the scope-side connector 13 is engaged with and connected to the extracorporeal-side connector 14. The scope-side connector 13 is configured such that, at this time, it is able to rotate around the axis C1 relative to the extracorporeal-side connector 14.

When the scope-side connector 13 and the extracorporeal-side connector 14 which are shown in FIG. 5 and FIG. 6 are connected together, they are in the following state. The first scope-side signal connecting portion D1 is disposed within the inside-cylinder space S1 of the first extracorporeal-side signal connecting portion D6, and the transmission ring 18a is electrostatically coupled with the reception ring 20a. The first scope-side signal connecting portion D2 is disposed within the inside-cylinder space S2 of the first extracorporeal-side signal connecting portion D7, and the reception ring 20b is electrostatically coupled with the transmission ring 18b. The scope-side power connecting portion D3 is disposed within the inside-cylinder space S3 of the extracorporeal-side power connecting portion D8, and the secondary coil ring 35 is electromagnetically coupled with the primary coil ring 36. The second scope-side signal connecting portion D4 is disposed within the inside-cylinder space S4 of the second extra corporeal-side signal connecting portion D9, and the transmission ring 19a is electrostatically coupled with the reception ring 21a. Furthermore, the second scope-side signal connecting portion D5 is disposed within the inside-cylinder space S5 of the second extracorporeal-side signal connecting portion D10, and the reception ring 21b is electrostatically coupled with the transmission ring 19b.

In addition, as is shown in FIG. 4, when the scope-side connector 13 and the extracorporeal-side connector 14 are connected together, the end surface of the scope-side light guide 53 and the end surface of the extracorporeal-side light guide 58 are positioned facing each other. As a result of this, illumination light is able to be transmitted from the extracorporeal-side light guide 58 to the scope-side light guide 53.

Next, operation of each portion of the signal transmitter 15a will be described.

Figure 7:
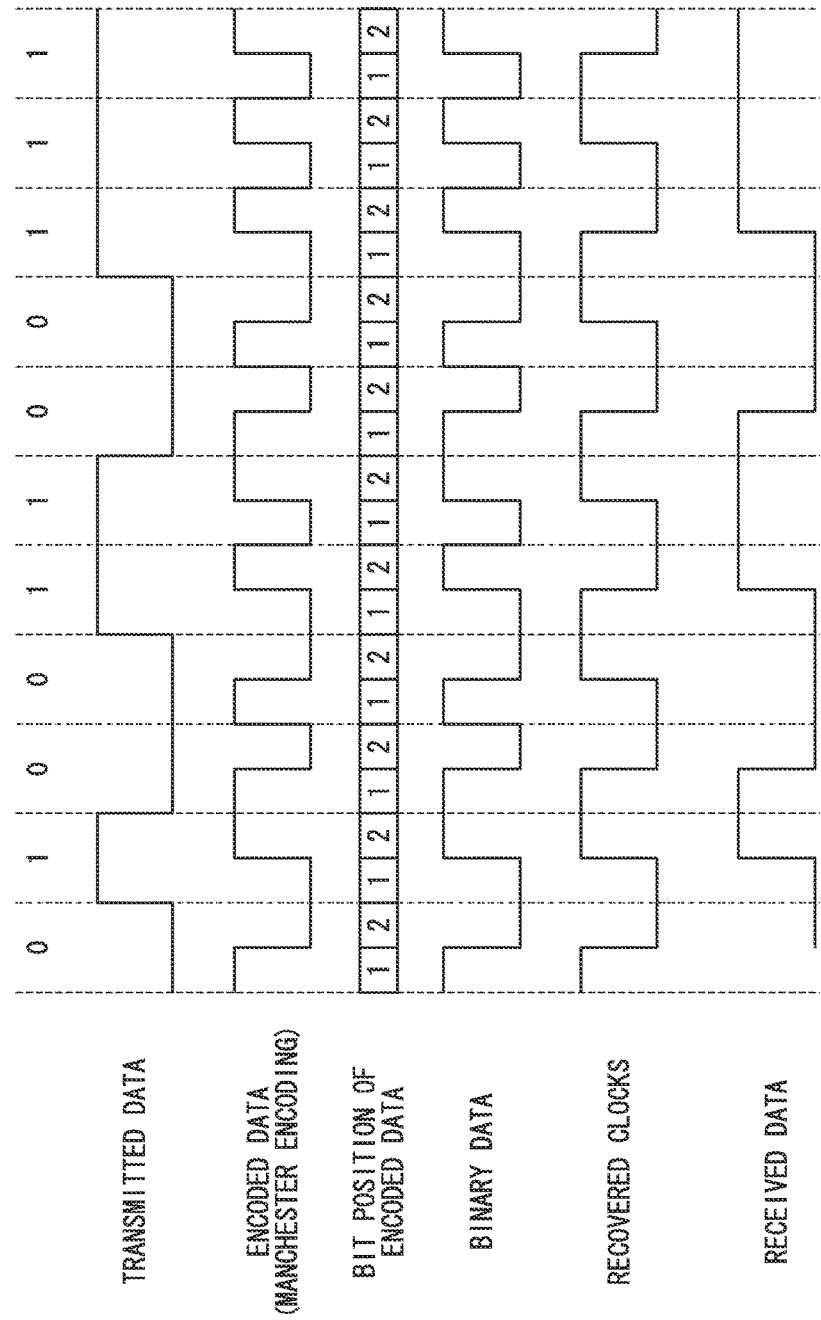
FIG. 7 is a timing diagram showing signal transmission operations of the signal transmitter of this signal transmitting device.

As is shown in FIG. 3 and FIG. 7, transmitted data which are in the form of digital signals transmitted from the A/D conversion circuit 28 undergo Manchester encoding in the modulation circuit 39a, and each transmitted data item is modulated into two bits which are expressed at the level of either "1" or "0", so as to create encoded data. This encoded data is then transmitted to the driver circuit 40a, and the driver circuit 40a creates opposite phase data relative to the encoded data.

The encoded data is transmitted to the reception ring 20a via the electrostatic coupling between the transmission ring 18a and the reception ring 20a. The opposite phase data is transmitted to the reception ring 21a via the electrostatic coupling between the transmission ring 19a and the reception ring 21a. The binarization circuit 45a then detects differences in level between the transmitted encoded data and opposite phase data, so that, as a result, it removes noise that is contained in common in both data. It also creates binary data in which the level of each bit is expressed as either "1" or "0". The binary data is transmitted to the clock recovery circuit 46a and the demodulation circuit 47a. In the clock recovery circuit 46a, recovery clocks are created using the timings of switches between a first bit and a second bit. The recovery clocks are transmitted to the demodulation circuit 47a, and based on these recovery clocks, the demodulation circuit 47a performs demodulation on the encoded data so as to create received data.

Next, a step in which signals and the like are transmitted between the endoscope scope insertion portion 4 and the extracorporeal device 5 will be described. Firstly, a step in which signals and power are transmitted from the extracorporeal device 5 to the endoscope scope insertion portion 4 (i.e., in a downlink direction) will be described.

As is shown in FIG. 2, the system control device 33 is connected to each of the downlink transmitter 16b, the uplink receiver 17a, the primary coil drive circuit 34, and the display unit 12.

When the system control device 33 transmits a signal which controls the CCD 3 to the downlink transmitter 16b, this control signal is encoded in the downlink transmitter 16b, and encoded data and opposite phase data relative to this encoded data are created. These data are transmitted via electrostatic coupling between the transmission ring 18b and reception ring 20b, and between the transmission ring 19b and reception ring 21b respectively, and are then decoded in the downlink receiver 17b.

The decoded control signals are then transmitted to the CCD drive circuit 26 which is connected to the downlink receiver 17b. The CCD drive circuit 26 controls the CCD 3 to which it is connected based on these control signals.

In contrast, when the system control device 33 transmits a control signal to the primary coil drive circuit 34, predetermined alternating current is supplied to the primary coil ring 36 which is electrically connected to the primary coil drive circuit 34. As a result, alternating current is supplied to the secondary coil ring 35 via electromagnetic coupling between the primary coil ring 36 and the secondary coil ring 35. This alternating current is then supplied to the rectifier circuit 29 which is electrically connected to the secondary coil ring 35, and is converted into direct current. The converted direct current then undergoes voltage adjustments in the DC/DC converter 30 which is connected to the rectifier circuit 29, and is supplied to the CCD drive circuit 26 and the like.

Next, a step in which a signal is transmitted from the endoscope scope insertion portion 4 to the extracorporeal device 5 (i.e., in an uplink direction) will be described.

A video signal acquired by the CCD 3 is transmitted to the video signal processing circuit 27 to which the CCD 3 is connected where it is processed so that an analog signal is created. This analog signal is then converted into a digital signal in the A/D conversion circuit 28 which is connected to the video signal processing circuit 27. The converted digital signal is then transmitted to the uplink transmitter 16a which is connected to the A/D conversion circuit 28.

The video signal transmitted to the uplink transmitter 16a is encoded so as to create encoded data and opposite phase data relative to this encoded data. These data are transmitted by means of the electrostatic coupling between the transmission ring 18a and reception ring 20a, and between the transmission ring 19a and reception ring 21a respectively, and are then decoded in the uplink receiver 17a.

The decoded video signal is then transmitted from the uplink receiver 17a to the system control device 33 where it is processed. It is then sent to the display unit 12 and is displayed.

In this manner, according to the endoscope system 1 of the first embodiment of the present invention, the transmission ring 18a and reception ring 20b, as well as the reception ring 20a and transmission ring 18b which are positioned facing the rings 18a and 20b respectively are all formed in a circular cylindrical shape, and are disposed so as to extend along the axis C1.

Accordingly, even if it is necessary to increase the surface area of the transmission rings 18a and 18b and the reception rings 20a and 20b, by placing these rings 18a, 18b, 20a, and 20b such that they extend further in the direction of the axis C1, it is possible to prevent the outer diameter of each of the first extracorporeal-side signal connecting portions D6 and D7 and first scope-side signal connecting portions D1 and D2 from increasing in size. In addition, it becomes possible to reliably transmit signals between the transmission ring 18a and reception ring 20a, and between the reception ring 20b and transmission ring 18b which are electrostatically coupled together.

Moreover, compared with the first scope-side signal connecting portion D6 which is placed within the inside-cylinder space S1, it is possible to decrease surface irregularities and surface area on the exterior and interior surfaces of the first scope-side signal connecting portion D1 which is provided on the endoscope scope insertion portion 4 which has the insertion portion 2 to which body fluids of an organism and the like are easily adhered. Accordingly, it is possible to easily clean the endoscope scope insertion portion 4 side.

Moreover, when the scope-side connector 13 and the extracorporeal-side connector 14 are connected together, the primary coil ring 36 which is provided on the extracorporeal-side power connecting portion D8 is electromagnetically coupled with the secondary coil ring 35 which is provided on the scope-side power connecting portion D3 which is placed within the inside-cylinder space S3 of this extracorporeal-side power connecting portion D8.

In this state, when AC voltage is supplied to the primary coil ring 36, induced electromotive force is generated in the secondary coil ring 35 by mutual induction. Accordingly, power can be supplied from the extracorporeal device 5 to the endoscope scope insertion portion 4.

Moreover, the transmission ring 19a and reception ring 21b, as well as the reception ring 21a and transmission ring 19b which are positioned facing the rings 19a and 21b respectively are all formed in a circular cylindrical shape, and are disposed so as to extend along the axis C1.

Accordingly, even if it is necessary to increase the surface area of the transmission rings 19a and 19b and the reception rings 21a and 21b, by placing these rings 19a, 19b, 21a, and 21b such that they extend further in the direction of the axis C1, it is possible to prevent the outer diameter of each of the second extracorporeal-side signal connecting portions D9 and D10 and the second scope-side signal connecting portions D4 and D5 from increasing in size.

In addition, it becomes possible to transmit encoded data between the transmission ring 18a and reception ring 20a, and to transmit opposite phase data of this encoded data between the transmission ring 19a and reception ring 21a both of which are electrostatically coupled together, and by detecting differences in level between these data, it is possible to reduce noise that is contained in common in both signals and to more reliably detect these signals.

Moreover, because the scope-side connector 13 is configured such that it is able to rotate around the axis C1 relative to the extracorporeal-side connector 14, it is possible to improve the ease of handling of the endoscope scope insertion portion 4.

In addition, the scope-side covering component 51 and the extracorporeal-side covering component 57 are provided respectively on the surface of the scope-side connector 13 and the surface of the extracorporeal-side connector 14. Accordingly, it is possible to reliably insulate the transmission ring 18a and reception ring 20a, the reception ring 20b and transmission ring 18b, the transmission ring 19a and reception ring 21a, and the reception ring 21b and transmission ring 19b, each of which are electrostatically coupled together.

Moreover, because the covering components 51 and 57 are provided between electrodes which are electrostatically coupled together, compared with a case in which only air exists between these electrodes, it is possible to increase the stray capacitance between the two electrodes. Accordingly, it is possible to strengthen the electrostatic coupling between these electrodes and thereby transmit signals more reliably.

In addition, by using solid dielectric materials such as the scope-side covering component 51 and the extracorporeal-side covering component 57, the respective distances between the transmission ring 18a and the reception ring 20a, between the reception ring 20b and the transmission ring 18b, between the transmission ring 19a and the reception ring 21a, and between the reception ring 21b and the transmission ring 19b can be stabilized so that it is possible to transmit signals with more stability.

Moreover, because the scope-side connector 13 and the extracorporeal-side connector 14 are all formed in a circular cylindrical shape, the scope-side light guide 53 and the extracorporeal-side light guide 58 can be positioned on the respective axes thereof. In addition, illumination light by these light guides 53 and 58 can be guided to an illumination device (not shown), and can be used to illuminate the distal end side of the insertion portion 2.

Furthermore, the signal connecting portions D1, D2, D4, D5, and the scope-side power connecting portion D3, and the signal connecting portions D6, D7, D9, D10, and the extracorporeal-side power connecting portion D8 are all placed at offset positions relative to each other in the direction of the axis C1. Accordingly, it is possible to prevent the outer diameters of the scope-side connector 13 and the extracorporeal-side connector 14 from increasing in size.

Note that in the present embodiment, the scope-side connector 13 and the extracorporeal-side connector 14 are all formed in a circular cylindrical shape.

However, the shape of the scope-side connector 13 and the extracorporeal-side connector 14 may also be a hollow elliptical shape or a hollow polygonal shape when viewed from the axial direction, or a portion of the side surface of the circular cylinder may be removed so as to form what is substantially a C shape when viewed from the axial direction.

Second Embodiment

Next, a second embodiment of the present invention will be described. Note that the same symbols are used for portions that are the same as those in the above described embodiment and any description of these is omitted. Only points of variance therewith are described.

Figure 8:
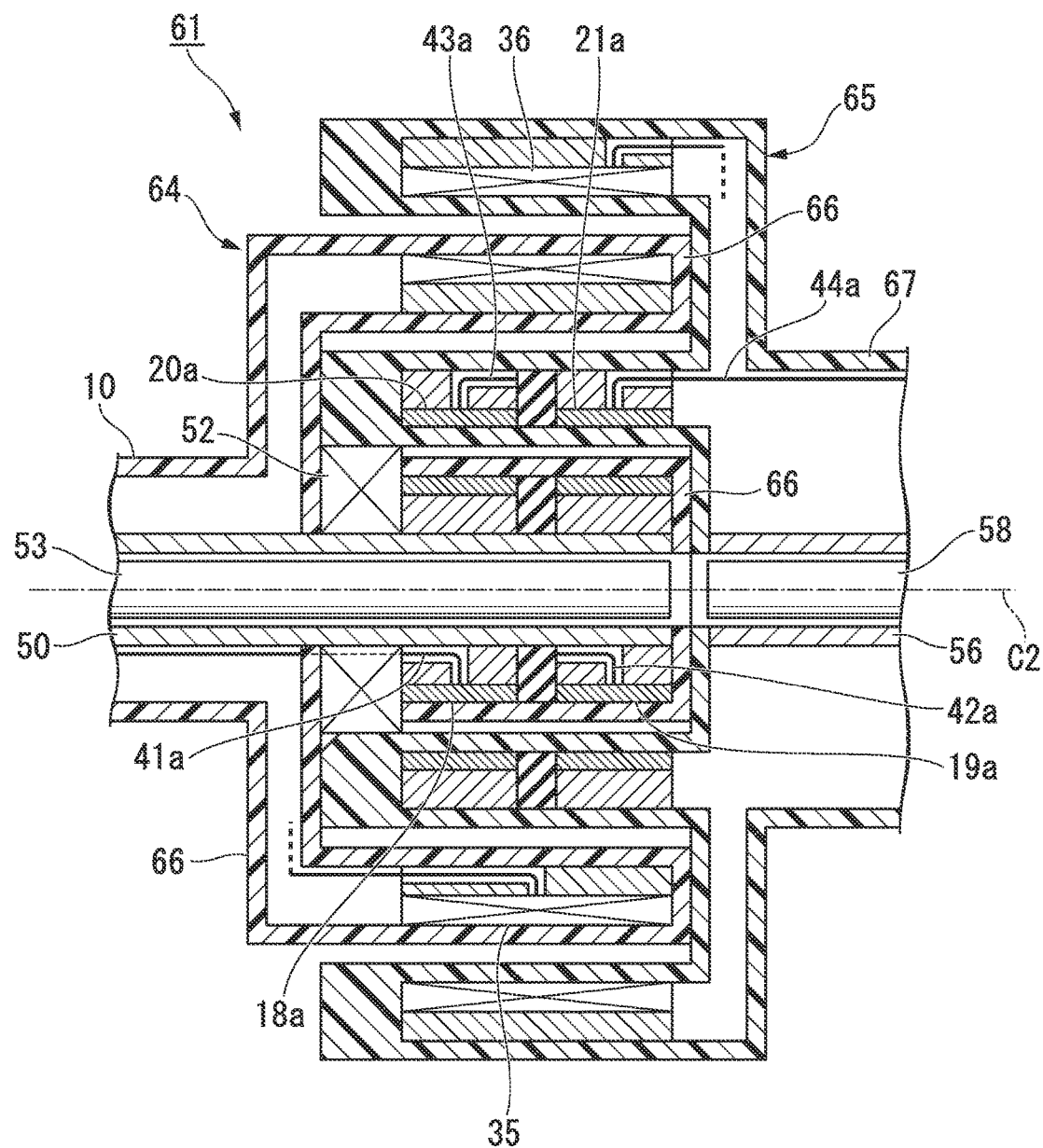
FIG. 8 is a cross-sectional view showing a state in which a scope-side connector and an extracorporeal-side connector of the first embodiment of the present invention are connected together.
Figure 9:
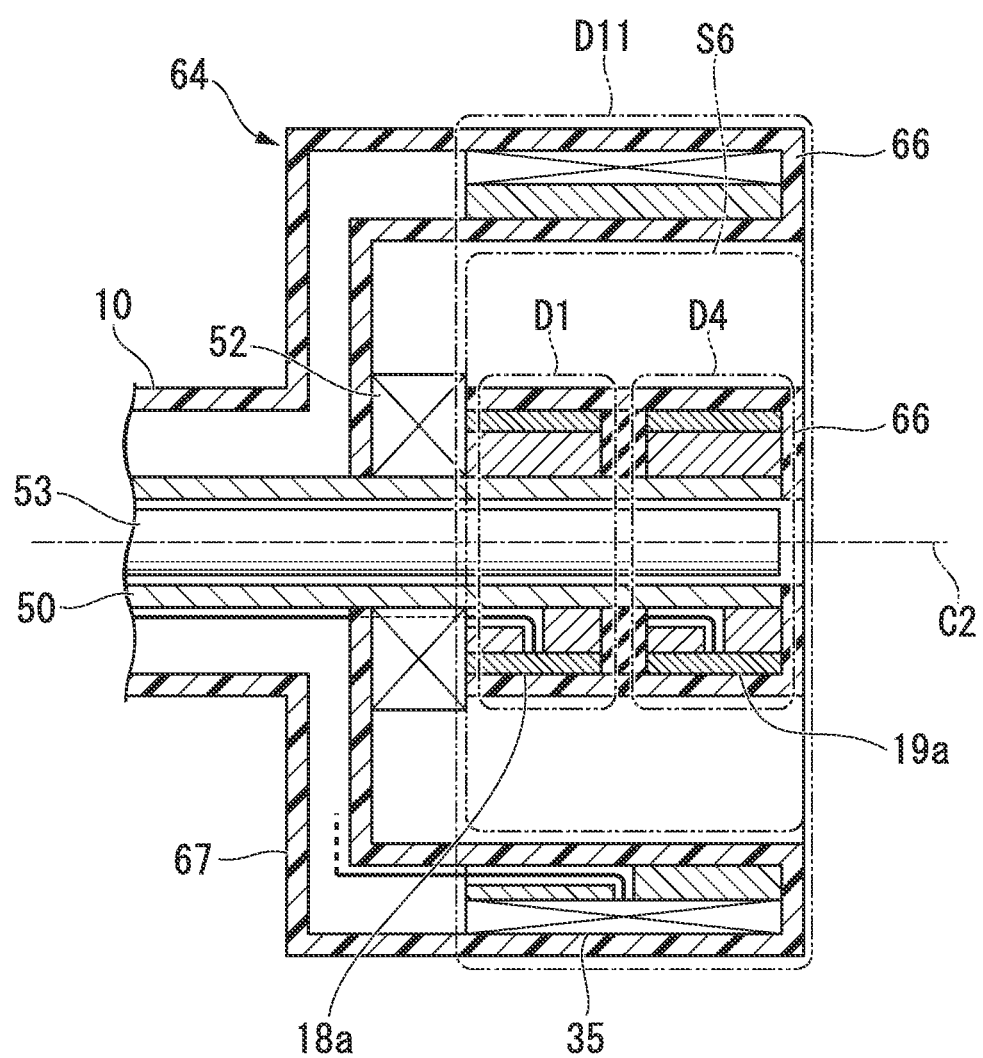
FIG. 9 is a cross-sectional view of the scope-side connector of this endoscope system.

In the present embodiment, as is shown in FIG. 8 and FIG. 9, in a scope-side connector 64 the secondary coil ring 35 is placed in a position which is separated towards the outer side in a radial direction from the transmission ring 18a and the transmission ring 19a. In addition, a supporting component which is formed from an insulating material is attached to each one of the transmission rings 18a and 19a and the secondary coil ring 35, and these transmission rings 18a and 19a and the secondary coil ring 35 are fixed on the inside of a scope-side covering component 66 which is formed from a dielectric material.

A fixed gap is provided between the transmission rings 18a and 19a, and the secondary coil ring 35 so as to allow the reception rings 20a and 21a to be inserted therein.

Note that the first scope-side signal connecting portion and the second scope-side signal connecting portion which are used for the downlink direction are not provided on the scope-side connector 64 of the present embodiment.

Accordingly, in the scope-side connector 64 of the endoscope system 61 of the present embodiment, a scope-side power connecting portion D11 is formed in a circular cylindrical shape, and the first scope-side signal connecting portion D1 and the second scope-side signal connecting portion D4 are disposed within the inside-cylinder space S6 of the scope-side power connecting portion D11. In other words, the scope-side power connecting portion D11 is positioned coaxially with the first scope-side signal connecting portion D1 and the second scope-side signal connecting portion D4 without its position being offset in the direction of the axis C2 of the first scope-side signal connecting portion D1 (i.e., the axis of the cylinder).

Figure 10:
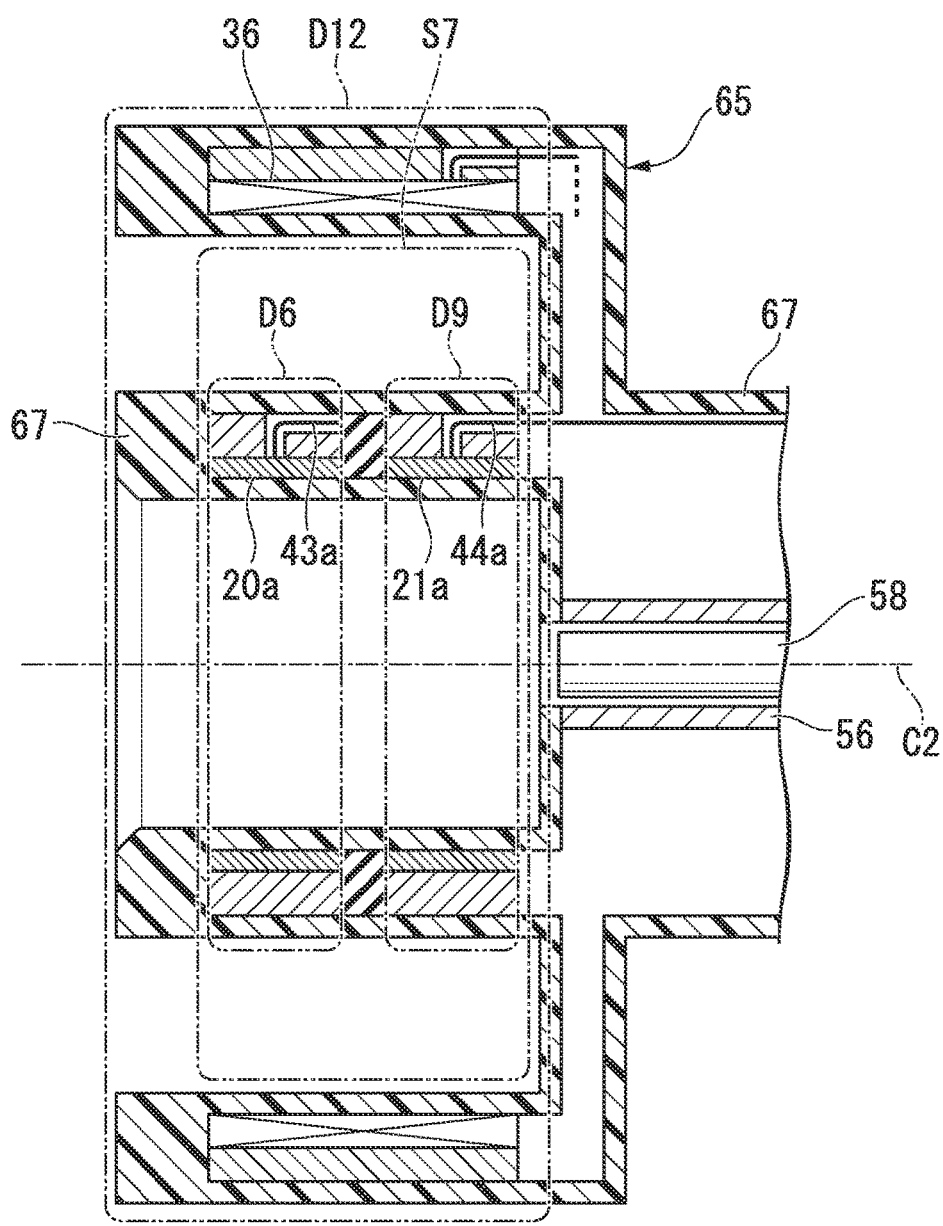
FIG. 10 is a cross-sectional view of the extracorporeal-side connector of this endoscope system.

Moreover, as is shown in FIG. 8 and FIG. 10, in an extracorporeal-side connector 65 the primary coil ring 36 is placed in a position which is separated towards the outer side in a radial direction from the reception ring 20a and the reception ring 21a. In addition, a supporting component which is formed from an insulating material is attached to each one of the reception rings 20a and 21a and to the primary coil ring 36, and these reception rings 20a and 21a and the primary coil ring 36 are fixed on the inside of an extracorporeal-side covering component 67 which is formed from a dielectric material.

A fixed gap is provided between the reception rings 20a and 21a, and the primary coil ring 36 so as to allow the secondary coil ring 35 to be inserted therein.

Note that the first extracorporeal-side signal connecting portion and the second extracorporeal-side signal connecting portion which are used for the downlink direction are not provided on the extracorporeal-side connector 65 of the present embodiment.

Accordingly, in the extracorporeal-side connector 65 of the endoscope system 61 of the present embodiment, the first extracorporeal-side signal connecting portion D6 and the second extracorporeal-side signal connecting portion D9 are disposed within the inside-cylinder space S7 of an extracorporeal-side power connecting portion D12. In other words, the extracorporeal-side power connecting portion D12 is positioned coaxially with the first extracorporeal-side signal connecting portion D6 and the second extracorporeal-side signal connecting portion D9 without its position being offset in the direction of the axis C2 (i.e., the axis of the cylinder).

The endoscope system 61 which is constructed in the manner described above is provided with the scope-side power connecting portion D11 and the extracorporeal-side power connecting portion D12, and even when power is supplied between the extracorporeal device 5 and the endoscope scope insertion portion 4, it is possible to shorten the overall length in the direction of the axis C2 of the first scope-side signal connecting portion D1 and the scope-side power connecting portion D11. In other words, the respective lengths of the scope-side connector 64 and the extracorporeal-side connector 65 in the direction of the axis C2 can be shortened.

Moreover, by positioning the primary coil ring 36 and the secondary coil ring 35 on the outer side in a radial direction, it is possible to secure a broader surface area where the primary coil ring 36 and the secondary coil ring 35 are electromagnetically coupled, and thereby enable the power transmitted between the primary coil ring 36 and the secondary coil ring 35 to be increased.

According to this invention, there are provided a scope-side power connecting portion and an extracorporeal-side power connecting portion, and even when power is supplied between the extracorporeal device and the endoscope scope insertion portion, it is possible to shorten the overall length of the first scope-side signal connecting portion and the scope-side power connecting portion in the axial direction thereof.

The first embodiment and the second embodiment of the present invention have been described above in detail with reference made to the drawings, however, the specific structure thereof is not limited to these embodiments, and various modifications and the like to the structure may be included therein insofar as they do not depart from the spirit or scope of the present invention.

For example, in the above described first embodiment and second embodiment, polycarbonate is used for the scope-side covering component and the extracorporeal-side covering component. However, it is also possible for the scope-side covering component and the extracorporeal-side covering component to be formed from a solid or liquid material whose relative dielectric constant is greater than 1. Furthermore, it is also possible for either the scope-side covering component or the extracorporeal-side covering component to be omitted.

Moreover, in the above described first embodiment and second embodiment, the signals are modulated and Manchester encoding is performed. However, the method used for the signal modulation is not limited to this and another modulation method may also be used.

Moreover, in the above described first embodiment and second embodiment, if a battery or the like is mounted in the endoscope scope insertion portion 4 and power is supplied from this battery to the CCD drive circuit 26 and the like, then it is not necessary to provide the scope-side power connecting portion and the extracorporeal-side power connecting portion in the scope-side connector and the extracorporeal-side connector.

Furthermore, in the above described first embodiment and second embodiment, if there is a low level of noise during the transmission of the signals, then it is possible for the transmission ring 19a and the reception ring 21a to be omitted.

According to the endoscope system of the present invention, cleaning is made easier, and the outer diameter of the signal connecting portion is prevented from being increased even when it is necessary to secure a large electrode surface area for the electrostatic coupling.

What is claimed is:

1. An endoscope system comprising:
an endoscope scope insertion portion having an insertion portion that is configured to be inserted inside a living organism and is provided with an observation device which is capable of making observations on the distal end side thereof;
an extracorporeal device which is disposed outside the living organism;
a first scope-side signal connecting portion that is provided on the endoscope scope insertion portion and has a first electrode which comprises a first transmit ring and a first reception ring electrically connected to the endoscope scope insertion portion; and
a cylindrical first extracorporeal-side signal connecting portion having an inside-cylinder space, that is provided on the extracorporeal device and has a second electrode which comprises a second transmit ring and a second reception ring electrically connected to the extracorporeal device, the first extracorporeal-side signal connecting portion configured to engage with the first scope-side signal connecting portion, wherein
the first scope-side signal connecting portion has a first side surface surrounding the axis of the inside-cylinder space,
the first electrode is located along the first side surface,
the inside-cylinder space has a second side surface surrounding the axis of the inside-cylinder space,
the second electrode is located along the second side surface, and
when the first scope-side signal connecting portion is engaged with the first extracorporeal-side signal connecting portion, at least a portion of the first side surface faces the second side surface, so that the first electrode and the second electrode are opposed in a radial direction of the inside-cylinder space and electrostatically coupled together, wherein the first transmit ring and the first reception ring are located within an inside-cylinder space of the second reception ring and the second transmit ring respectively, wherein the first transmit ring and the first reception ring are coaxially-arranged on the axis and have same diameter, and wherein the second transmit ring and the second reception ring are coaxially-arranged on the axis and have same diameter.

2. The endoscope system according to claim 1, further comprising:
a scope-side power connecting portion that is provided on the endoscope scope insertion portion and has a first coil which is electrically connected to the endoscope scope insertion portion; and
a cylindrical extracorporeal-side power connecting portion that is provided on the extracorporeal device and has a second coil which is electrically connected to the extracorporeal device, the extracorporeal-side power connecting portion configured to engage with the scope-side power connecting portion, wherein
when the scope-side power connecting portion is engaged with the extracorporeal-side power connecting portion, at least a portion of the scope-side power connecting portion is located within an inside-cylinder space of the extracorporeal-side power connecting portion, so that the first coil and the second coil are electromagnetically coupled together.

3. The endoscope system according to claim 2, wherein the scope-side power connecting portion is formed in a cylindrical shape, and has an inside-cylinder space formed inside it, and
the first scope-side signal connecting portion is disposed outside the inside-cylinder space of the scope-side power connecting portion.

4. The endoscope system according to claim 2, wherein the scope-side power connecting portion is formed in a cylindrical shape, and has an inside-cylinder space formed inside it, and
either all of or a portion of the first scope-side signal connecting portion is disposed within the inside-cylinder space of the scope-side power connecting portion.

5. The endoscope system according to claim 1, further comprising:
a second scope-side signal connecting portion that is provided on the endoscope scope insertion portion and has a third electrode which is electrically connected to the endoscope scope insertion portion; and
a cylindrical second extracorporeal-side signal connecting portion that is provided on the extracorporeal device and has a fourth electrode which is electrically connected to the extracorporeal device, the second extracorporeal-side signal connecting portion configured to engage with the second scope-side signal connecting portion, wherein
when the second scope-side signal connecting portion is engaged with the second extracorporeal-side signal connecting portion, at least a portion of the second scope-side signal connecting portion is located within an inside-cylinder space of the second extracorporeal-side signal connecting portion, so that the third electrode and the fourth electrode are electrostatically coupled together, and
signals that are based on the electrostatic coupling between the third electrode and the fourth electrode have an opposite phase relative to signals that are based on the electrostatic coupling between the first electrode and the second electrode.

6. The endoscope system according to claim 1, wherein the endoscope scope insertion portion is configured such that it is able to rotate around the axis of the first extracorporeal-side signal connecting portion relative to the extracorporeal device.

7. The endoscope system according to claim 1, wherein there is further provided a solid or liquid dielectric material whose relative dielectric constant is greater than 1, and
when the first scope-side signal connecting portion and the first extracorporeal-side signal connecting portion are engaged with each other, the dielectric material is located between the first electrode and the second electrode.

8. The endoscope system according to claim 1, wherein the first scope-side signal connecting portion is formed in a cylindrical shape, and has an inside-cylinder space formed inside it.

9. The endoscope system according to claim 8, wherein there is further provided a light guide which is inserted in the inside-cylinder space of the first scope-side signal connecting portion.

* * * * *